(12) United States Patent
Ji

(10) Patent No.: US 9,556,427 B2
(45) Date of Patent: Jan. 31, 2017

(54) METHODS AND COMPOSITIONS FOR PREPARATION OF NUCLEIC ACIDS

(71) Applicant: SYNGENTA PARTICIPATIONS AG, Basel (CH)

(72) Inventor: Yanshan Ji, Durham, NC (US)

(73) Assignee: Syngenta Participations AG, Basel (CH)

( * ) Notice: Subject to any disclaimer, the term of this patent is extended or adjusted under 35 U.S.C. 154(b) by 39 days.

(21) Appl. No.: 14/171,816

(22) Filed: Feb. 4, 2014

(65) Prior Publication Data

US 2014/0242594 A1   Aug. 28, 2014

Related U.S. Application Data

(60) Provisional application No. 61/769,925, filed on Feb. 27, 2013.

(51) Int. Cl.
  *C07H 21/00* (2006.01)
  *G01N 1/34* (2006.01)
  *C12N 15/10* (2006.01)

(52) U.S. Cl.
  CPC .................. *C12N 15/1003* (2013.01)

(58) Field of Classification Search
  CPC ......... C12Q 1/68; C12Q 1/686; C12Q 1/6806; C07H 21/00; G01N 1/34; C12P 19/34
  See application file for complete search history.

(56) References Cited

U.S. PATENT DOCUMENTS

| | | | | |
|---|---|---|---|---|
| 4,900,667 A * | 2/1990 | Arena | ...................... | C07H 3/02 435/128 |
| 4,935,342 A * | 6/1990 | Seligson | .................. | C07H 1/08 435/270 |
| 5,234,809 A * | 8/1993 | Boom | .................... | C07H 21/00 422/504 |
| 6,111,096 A * | 8/2000 | Laugharn, Jr. | ........ | B01L 3/5027 203/1 |
| 6,180,778 B1 * | 1/2001 | Bastian | .............. | C12N 15/1006 536/25.3 |
| 7,727,718 B2 | 6/2010 | Chomczynski | | |
| 2001/0041337 A1 * | 11/2001 | Szyf | ........................ | C07H 21/00 435/6.13 |
| 2001/0042256 A1 * | 11/2001 | Clark | ................. | A01K 67/0275 800/7 |
| 2001/0051610 A1 * | 12/2001 | Bennett | .................. | C12N 15/87 514/44 R |
| 2002/0025561 A1 * | 2/2002 | Hodgson | ................ | C12N 15/66 435/91.1 |
| 2003/0104973 A1 * | 6/2003 | Einat | ...................... | C07K 14/47 514/1 |
| 2003/0170664 A1 * | 9/2003 | Mori | .................. | C12N 15/1006 435/6.12 |
| 2004/0053230 A1 * | 3/2004 | Schaffer | ............... | C12Q 1/6851 435/6.12 |
| 2004/0209283 A1 * | 10/2004 | Yagi | ....................... | C12Q 1/707 435/6.12 |
| 2005/0014245 A1 * | 1/2005 | Hebel | ................. | B01F 13/0255 435/270 |
| 2005/0026177 A1 * | 2/2005 | Urthaler | ............. | C12N 15/1006 435/5 |
| 2005/0118593 A1 | 6/2005 | Potocki et al. | | |
| 2006/0166331 A1 * | 7/2006 | Au-Yeung | ................ | B03D 3/06 435/91.1 |
| 2006/0288439 A1 * | 12/2006 | Chan | .................. | C12N 15/8225 800/278 |
| 2008/0249287 A1 * | 10/2008 | Rossomando | ....... | C07K 14/495 530/408 |
| 2009/0004716 A1 * | 1/2009 | Draghia-Akli | ..... | C12N 15/1017 435/170 |
| 2009/0227011 A1 | 9/2009 | Chen | | |
| 2009/0239216 A1 * | 9/2009 | Sasatsu | .............. | C07K 16/1275 435/6.16 |
| 2009/0275088 A1 * | 11/2009 | Templeton | ......... | C12N 15/1003 435/91.4 |
| 2010/0279282 A1 * | 11/2010 | Liang | ................... | C12Q 1/6895 435/6.12 |
| 2014/0242584 A1 | 8/2014 | Ji et al. | | |

OTHER PUBLICATIONS

Birnboim, A Rapid Alkaline Extraction Method for the Isolation of Plasmid DNA. Methods in Enzymology 100: 243 (1983).*
Burstain et al., Sensitive detection of Treponema pallidum by using the polymerase chain reaction. Journal of Clinical Microbiology 29 (1) : 62 (1991).*
French et al., HyBeacon probes: a new tool for DNA sequence detection and allele discrimination. Molecular and Cellular Probes 15 : 363 (2001).*
John, An efficient method for isolation of RNA and DNA from plants containing polyphenolics. Nucleic Acids Research 20(9) : 2381 (1992).*

(Continued)

*Primary Examiner* — Ethan C Whisenant
(74) *Attorney, Agent, or Firm* — Dale Skalla

(57) ABSTRACT

A method for isolating genomic DNA (gDNA) from a biological material. In some embodiments, the method includes (a) contacting a sample that contains gDNA with a solution of hydroxide and a detergent under conditions and for a time sufficient to degrade a cell wall, a cell membrane, a nuclear membrane, a nucleoprotein, or combinations thereof and/or to denature the gDNA; (b) mixing into the solution resulting from step (a) a solution characterized by high salt and sufficient buffering capacity to reduce the pH of the solution to less than 10, thereby producing a neutralized solution; (c) centrifuging the sample at a speed and length of time sufficient to clarify the preparation; and (d) removing insoluble material from the neutralized and clarified preparation, whereby a solution of gDNA is produced. Also provided are method for performing a quantitative polymerase chain reaction (qPCR) of a gDNA sample, methods for performing genotyping or other molecular marker analysis of a gDNA sample, and methods for determining a haplotype of a cell.

15 Claims, 1 Drawing Sheet

(56) References Cited

OTHER PUBLICATIONS

Kunkel et al.,.Analysis of human Y-chromosome-specific reiterated DNA in chromosome variants. PNAS 74 (3) : 1245 (1977).*
Rasmussen et al., Quantitation of minimal residual disease in multiple myeloma using an allele-specific real-time PCR assay. Experimental Hematology 28 : 1039 (2000).*
Shi et al., Antigen Retrieval Techniques: Current Perspectives. Journal of Histochemistry & Cytochemistry 49(8) : 931 (2001).*
Shi et al., DNA Extraction from Archival Formalin-fixed, Paraffin-embedded Tissue Sections Based on the Antigen Retrieval Principle: Heating Under the Influence of pH. Journal of Histochemistry & Cytochemistry 49(8) : 931 (2001).*
Shi et al., DNA extraction from archival formalin-fixed, paraffin-embedded tissues: heat-induced retrieval in alkaline solution. Histochemistry Cell Biology 122 : 211 (2004).*
Truett et al., Preparation of PCR Quality Mouse Genomic DNA with Hot Sodium Hydroxide and Tris (HotSHOT). Biotechniques 29 : 52 (2000).*
Yang et al., Identification and quantification of three genetically modified insect resistant cotton lines using conventional and Taq-Man real-time polymerase chain reaction methods. Journal of Agricultural and Food Chemistry 53 : 6222 (2005).*
Davis et al. Basic Methods in Molecular Biology pp. 99-101 (1986).*
Suda et al., "Use of real-time RT-PCR for the detection of allelic expression of an imprinted gene" International Journal of Molecular Medicine 12:243-246 (2003).
Notification of Transmittal of the International Search Report and the Written Opinion of the International Searching Authority, or the Declaration in PCT Application No. PCT/US14/15474 mailed May 21, 2014 (11 pages).
Del Serrone et al., "Importance of the vegetative stage for phytoplasma detection in yellow-diseased grapevines" Vitus 35(2):101-102 (1996).
Andre et al., "Haplotype Analysis using a Novel Real-Time Amplification Strategy on the MJ Research Opticon Continuous Fluorescence Detection System" MJ Research, Inc. 2004, Poster #P134 (1 page).
Scherzinger et al., "In vitro characterization of a carotenoid cleavage dioxygenase from *Nostoc* sp. PCC 7120 reveals a novel cleavage pattern, cytosolic localization and induction by highlight" Molecular Microbiology (2008) 69(1): 231-244.
Moore et al., "Purification and Concentration of DNA from Aqueous Solutions" Current Protocols in Molecular Biology (2002) 2.1.1-2.1.10.
Strauss, "Preparation of Genomic DNA from Mammalian Tissue" Current Protocols in Molecular Biology (1998) 2.2.1-2.2.3.
Qiagen, "The QIAGEN Bench Guide" U.S.A. 2001 (8 pages).
International Search Report for International Application No. PCT/US2014/072151 mailed Apr. 29, 2015.
Anuradha et al., Emirates Journal of Food and Agriculture, 25, 2, 124-131, 2012.
RNeasy Mini Handbook, Sep. 2010, 80 pages total.
Yun et al., Nucleic Acids Research, 34, 12, 1-10, Jul. 13, 2006.
Fang et al., "A Quick and Inexpensive Methodd for Removing Polysaccharides from Plant Genomic DNA," BioTechniques, Jul. 1992, vol. 13, No. 1, Aug. 1992, pp. 52-54, 56.
Rogers et al., "Extraction of DNA from Milligram Amounts of Frest, Herbarium and Mummified Plant Tissues," Plant Molecular Biology Issue 69, pp. 69-76, May 1985.
Porebski, et al., "Modification of a CTAB DNA Extraction Protocol for Plants Containing High Polysaccharide and Polyphenol Components," Plant Molecular Biology Reporter, vol. 15, Issue 1, Mar. 1997, pp. 8-15.
Lodhi et al.,"A Simple and Efficient Method for DNA Extraction from Grapevine Cultivars and *Vitis* Species," Plant Molecular Biology Reporter, vol. 12, Issue 1, pp. 6-13, Mar. 1994.
Birnboim et al., "A rapid alkaline extraction procedure for screening recombinant plasmid DNA," Nucleic Acids Research, vol. 7, No. 6, Aug. 1979.
Wan et al., "A Modified Hot Borate Method Significantly Enhances the Yeild of High-Quality RNA from Cotton (*Gossypium hirsutum* L.)," Analytical Biochemistry, vol. 223, pp. 7-12, Oct. 1993.
Chang et al.. "A Simple and Efficient Method for Isolating RNA from Pine Trees," Plant Molecular Biology, vol. 11, Issue 2, Jun. 1993.

* cited by examiner

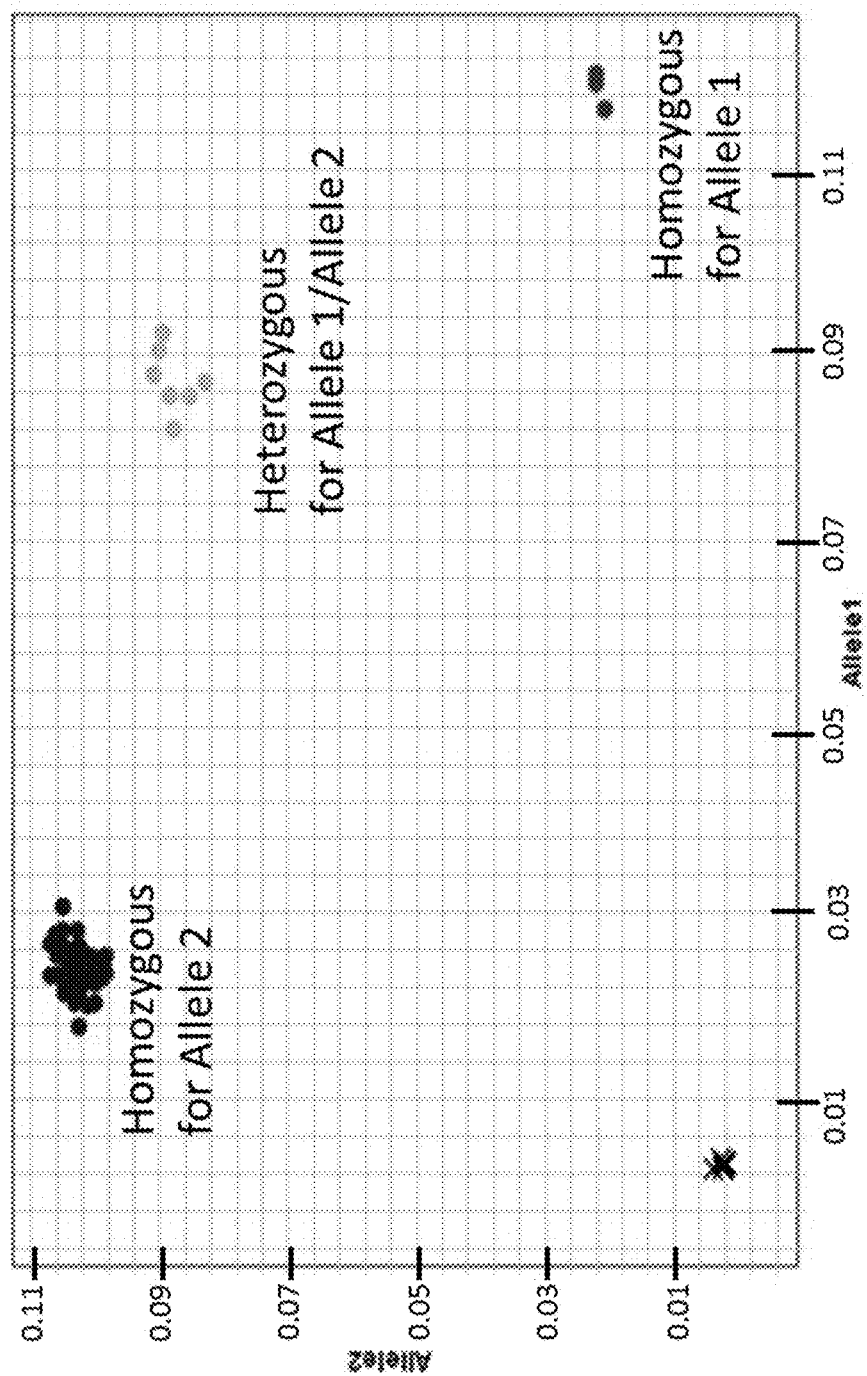

SEQUENCE LISTING

<160> NUMBER OF SEQ ID NOS: 2

<210> SEQ ID NO 1
<211> LENGTH: 23
<212> TYPE: DNA

```
<213> ORGANISM: Zea mays

<400> SEQUENCE: 1
cgtcgtttcc catctcttcc tcc                                          23

<210> SEQ ID NO 2
<211> LENGTH: 20
<212> TYPE: DNA
<213> ORGANISM: Zea mays

<400> SEQUENCE: 2
ccactccgag accctcagtc                                              20
```

METHODS AND COMPOSITIONS FOR PREPARATION OF NUCLEIC ACIDS

TECHNICAL FIELD

The presently disclosed subject matter relates to methods, compositions, and kits for preparing nucleic acids. The nucleic acids prepared using the presently disclosed subject matter can be employed in high throughput (HT) analytical techniques including, but not limited to real-time quantitative PCR, qualitative PCR, isothermal amplification, molecular marker assisted breeding, SNP discovery, genotyping, and GMO detection. The presently disclosed subject matter can also be employed in low throughput and quick point-of-care diagnostic applications.

BACKGROUND

A goal of plant breeding is to combine, in a single plant, various desirable traits. For field crops such as corn, these traits can include greater yield and better agronomic quality. However, genetic loci that influence yield and agronomic quality are not always known, and even if known, their contributions to such traits are frequently unclear.

Once discovered, however, desirable genetic loci can be selected for as part of a breeding program in order to generate plants that carry desirable traits. An exemplary approach for generating such plants includes the transfer by introgression of nucleic acid sequences from plants that have desirable genetic information into plants that do not by crossing the plants using traditional breeding techniques. Desirable loci can be introgressed into commercially available plant varieties using marker-assisted selection (MAS) or marker-assisted breeding (MAB). MAS and MAB involve the use of one or more of the molecular markers for the identification and selection of those plants that contain one or more loci that encode desired traits. Such identification and selection can be based on selection of informative markers that are associated with desired traits.

However, even when desirable genetic loci are known, the analysis of the genomes of plants that carry the desirable genetic loci can be extremely time-consuming. Not only do samples need to be isolated from plants, but the genomic contents of the samples must be isolated and analyzed, usually individually and in isolation from all other such samples. Successful application of a genome analysis system thus typically requires pure, high-quality genomic DNA (gDNA), and having a highly specific, reproducible, and efficient method for preparing the same with quickly and with low cost would be desirable. It would be further desirable if such a system could be automated or otherwise designed for high-throughput applications.

Additionally, such a system should preferably remove any and all inhibitors of downstream analytical techniques that might be introduced into the gDNA sample. Sources of such inhibitors can include the preparation reagents themselves as well as components of the plant tissues and/or cells that remain in the isolated gDNA sample. In particular, isolation of plant gDNA frequently results in the presence of high levels of polysaccharides, polyphenols, pigments, and/or other secondary metabolites (see Wen & Deng, 2002), the presence of which can make gDNA preparations unusable in downstream analyses (see Michiels et al., 2003; Qiang et al., 2004).

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides in some embodiments methods for isolating gDNA from biological materials. In some embodiments, the methods comprise (a) contacting a sample comprising gDNA with a Solution A comprising hydroxide and a detergent under conditions and for a time sufficient to degrade a cell wall, a cell membrane, a nuclear membrane, or combinations thereof, and/or to denature the gDNA and proteins; (b) mixing into the solution resulting from step (a) a Solution B comprising high salt to precipitate polysaccharides and proteins and sufficient buffering capacity to reduce the pH of the solution to less than 10, thereby producing a neutralized and clarified preparation after centrifugation; and (c) removing insoluble material from the neutralized and clarified preparation by transferring the supernatant out, whereby a solution of gDNA is produced. In some embodiments, the sample comprises ground plant tissue, optionally ground leaf tissue, ground seeds, or ground grain. In some embodiments, Solution A comprises 0.2 M sodium hydroxide and 0.25-0.5% SDS (w/v). In some embodiments, Solution B comprises about 0.2 M Tris and 3-4.5 molar ammonium acetate. In some embodiments, the removing step comprises centrifuging the neutralized and clarified (e.g., precipitated) preparation for about 10 minutes at about 3200×g and the method further comprises transferring and diluting the supernatant comprising the gDNA that results from the centrifuging step.

In some embodiments, the presently disclosed methods further comprise adjusting the supernatant to 10 mM Tris and 1 mM EDTA (TE buffer).

In some embodiments, the presently disclosed methods further comprise adjusting the supernatant to a range of 0-50 mM Tris-HCl, pH 7-9 and/or 0-5 mM EDTA.

The presently disclosed subject matter also provides in some embodiments methods for performing quantitative polymerase chain reactions (qPCR) of gDNA samples. In some embodiments, the methods comprise (a) providing a gDNA sample prepared by the presently disclosed methods; and (b) performing PCR under conditions wherein the $C_T$ value can be collected in real-time for quantitative analysis, whereby qPCR of the gDNA sample is performed.

The presently disclosed subject matter also provides in some embodiments methods for performing SNP or other molecular marker analyses of gDNA samples. In some embodiments, the SNP or other molecular marker analyses of gDNA samples is performed on a gDNA samples prepared by the presently disclosed methods.

In some embodiments, the presently disclosed subject matter also provides methods for genotyping a gDNA sample. In some embodiments, the methods comprise (a) providing a gDNA sample prepared by a method as set forth herein; and (b) performing a SNP assay using at least two primers and two allele-specific probes, wherein end-point signal levels show zygosity status on a 2-D allelic discrimination plot.

In some embodiments, the presently disclosed subject matter also provides methods for determining a haplotype of a cell with respect to a gene of interest. In some embodiments, the methods comprise (a) providing a gDNA sample isolated from the cell prepared by a method as set forth herein, wherein the gDNA sample comprises gDNA comprising the gene of interest; (b) performing quantitative PCR (qPCR) on the gDNA sample with one or more nucleic acid reagents that are designed to discriminate between at least two alleles of the gene of interest; and (c) analyzing products from the qPCR, wherein a haplotype of the cell with respect to the gene of interest is determined. In some embodiments, the one or more nucleic acid reagents comprise at least two sets of oligonucleotide primers, a first set of which is specific for a first allele of the gene of interest and a second set of which is specific for a second allele of the gene of interest.

It is an object of the presently disclosed subject matter to provide methods, compositions, and kits for preparing nucleic acids.

An object of the presently disclosed subject matter having been stated hereinabove, and which is achieved in whole or in part by the presently disclosed subject matter, other objects will become evident as the description proceeds when taken in connection with the accompanying drawing and examples as best described herein below.

BRIEF DESCRIPTION OF THE DRAWING

FIG. 1 is a graph showing results of an allelic discrimination (SNP) assay. Using the Sequence Detection System (SDS) software, allele calls were made based on the fluorescence for the two dyes measured in each sample. The different locations on the plot represent different zygosity calls for the tested samples. The negative samples, which did not contain DNA, are shown as black crosses and represented as an "undetermined" result. The experimental results show that the majority of the seeds where homozygous for Allele 2, with 7 samples heterozygous for Alleles 1 and 2, and only a few samples homozygous for Allele 1. The discrete, tight clustering is indicative of the high quality of the DNA used for the reactions.

BRIEF DESCRIPTION OF THE SEQUENCE LISTING

SEQ ID NOs: 1 and 2 are the nucleotide sequences of exemplary oligonucleotide primers that can be employed (in some embodiments, employed together in a TAQMAN® Assay) to assess the expression of a *Zea mays* alcohol dehydrogenase gene product.

A Sequence Listing in ASCII text format, submitted under 37 C.F.R. §1.821, entitled "73688_ST25.txt", about 1 kilobytes in size, generated on Mar. 14, 2014 and filed via EFS-Web is provided in lieu of a paper copy. This Sequence Listing is hereby incorporated by reference into the specification for its disclosures.

DETAILED DESCRIPTION

I. General Considerations

Various techniques have been developed to isolate nucleic acids from cells and tissues of plants and animals. Exemplary methods for isolation of nucleic acids include those described in Sambrook & Russell, 2001; Ausubel et al., 1988; and Ausubel et al., 1999. A primary method employed for extracting genomic DNA (gDNA) from plants employs cetyltrimethylammonium bromide (CTAB) to precipitate nucleic acids and acidic polysaccharides from solutions of low ionic strength, but can also be used to remove polysaccharides and proteins from solutions of higher ionic strength (e.g., <0.7 M NaCl; see Sambrook & Russell, 2001; see also Murray & Thompson, 1980).

One of the drawbacks of the CTAB method, however, is that in order to recover the nucleic acids from high ionic strength solutions, a subsequent treatment with organic solvents and alcohol precipitation and/or purification over a cesium chloride gradient is typically required. Such steps are not desirable for a high-throughput method, not only because of the labor, time, and expense involved, but also because if these steps are not taken, the nucleic acid preparation is likely to be contaminated with various inhibitors of downstream analyses.

An alternative method for isolating plant gDNA is disclosed in Kotchoni & Gachomo (2009) *Mol Biol Rep* 36:1633-1636. This multi-step method involves grinding plant tissue, incubating the same in a mixture of sodium dodecyl sulfate (SDS) and sodium chloride, spinning down insoluble aggregates, transferring the nucleic acid-containing supernatant to a new vessel, isopropanol precipitation of nucleic acids, re-spinning down the precipitated nucleic acids, performing an ethanol wash, spinning down the washed nucleic acids yet again, drying the nucleic acids, and dissolving the same in a buffer of choice. Given the numerous steps and manipulations required, this method is also largely unsuitable for automation. Additionally, many inhibitors of DNA polymerases are typically present in the resuspended DNA, such that the DNA quality is generally not well suited for quantitative PCR.

A third method for isolating plant gDNA is disclosed in Dilworth & Frey (2000) *Plant Molecular Biology Reporter* 18:61-64. This method employs Proteinase K and a detergent (e.g., polysorbate 20), but requires several incubations at elevated temperatures (e.g., 65° C.). It avoids the alcohol precipitation steps of some of the other methods, but generally the DNA yield is low and quality is poor, leading to unreliable PCR performance even using "regular" (i.e., non-quantitative) PCR. Additionally, since proteinase K is the only reagent that can remove potential inhibitors, no protein inhibitors are typically present in the isolated DNA. The cost of the enzyme itself can negatively impact the usefulness of this method in a high-throughput process. Of course, high per-run costs are also associated with methods that are based on using solid supports such as silica-based supports or magnetic beads to isolate gDNA.

A final method for isolating plant gDNA is found in Porcar et al. (2007) *Journal of the Science of Food and Agriculture* 87:2728-2731. This method comprises grinding plant tissue in sodium hydroxide, centrifuging the resulting extract to remove insoluble aggregates, adding sodium acetate to the supernatant containing the nucleic acids, and re-centrifuging to recover the nucleic acids. While this method requires minimal manipulations, the DNA quality is generally quite poor (i.e., is not sufficiently high to be useful for quantitative PCR), and the vast majority of inhibitors remain in the DNA extracts.

In view of these methods, the presently disclosed subject matter provides a simple, fast, relatively inexpensive method for isolating plant gDNA that provides the plant gDNA in sufficient purity that it can be easily and reproducibly employed in molecular biological manipulations that require high purity nucleic acids.

Thus, disclosed herein are quick, simple, cheap, and high throughput gDNA (gDNA) extraction methods. The amount and quality of gDNA isolated are sufficiently high to make the presently disclosed methods suitable for quantitative analysis by real-time PCR. The particular components of the presently disclosed reagents have multiple functions in extracting high quality DNA by eliminating contaminants and inhibitors effectively. These functions include: 1) more efficient cell lysis and DNA release by the combination and synergy of alkali and SDS, and this also made the DNA easily accessible to primer and polymerase in PCR; 2) high salt to precipitate SDS-proteins, polysaccharides and other macromolecular complexes; 3) PVP and EDTA to remove polyphenols and stabilize the gDNA; and 4) avoidance of hazardous solvents, PCR inhibitory chemicals, and costly materials including but not limited to magnetic beads and/or other nucleic acid-binding resins.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the articles "a", "an", and "the" refer to "one or more" when used in this application, including in the claims. For example, the phrase "a symptom" refers to one or more symptoms. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the phrase "biological material" refers to biological materials in any matrix, including but not limited to tissue isolated from a living multi-cellular organism, a culture of single-celled organisms, a soil or water sample, a food or feed sample, animal, human, or plant tissue culture, clinic samples, seeds, and/or seed powder.

As used herein, the term "surfactant" refers to a compound which can act as a detergent. Surfactants that can be employed in the methods and compositions of the presently disclosed subject matter include, but are not limited to, sodium dodecyl sulfate (SDS), cetyltrimethylammonium bromide (CTAB), TRITON™ X-100, TWEEN®-20, NP-40, and 3-[(3-cholamidopropyl)dimethylammonio]-1-propanesulfonate (CHAPS).

As used herein the term "salt" refers to an ionic compound that results from a neutralization reaction of an acid and a base. Salts include, but are not limited to, sodium chloride, potassium chloride, ammonium chloride, sodium acetate, potassium acetate, and ammonium acetate.

III. Compositions and Methods for Isolation of gDNA

In some embodiments, the presently disclosed compositions have been designed to optimize gDNA extraction from plants, although the presently disclosed compositions can also be employed for gDNA extraction from other biological materials including but not limited to animal cells, tissues, and/or organs. In some embodiments, the compositions and methods that employ the same remove inhibitors of DNA polymerases that might be employed in downstream uses and the gDNA is isolated in sufficient amounts and purity that the gDNA can be employed in sensitive applications such as but not limited to quantitative PCR. In some embodiments, the compositions are employed in a high-throughput, automated gDNA extraction method.

The compositions of the presently disclosed subject matter comprise two main reagent solutions termed Solution A and Solution B. Solution A is an alkaline SDS solution, which is designed to lyse plant cells, denature cellular proteins, and release gDNA. While not wishing to be bound by any particular theory of operation, Solution A is also believed to bind to lipids and denatured proteins, especially nucleoprotein in the plant chromosomes.

Solution B is a buffered solution of high salt (e.g., at least about 3 M sodium acetate). The buffer is intended to lower the pH of the gDNA solution to in some embodiments less than about 9.5, in some embodiments less than about 9.0, in some embodiments less than about 8.5, in some embodiments less than about 8.0, and in some embodiments less than about 7.5. In some embodiments, the pH of the gDNA solution upon adding Solution B is about 7.0, 7.5, or 8.0.

The other components of Solution B provide additional benefits to the presently disclosed compositions and methods. While not wishing to be bound by any particular theory of operation, the high salt present in Solution B precipitates the SDS-bound proteins and likely also removes sugars and starches present in the plant cell lysate.

In some embodiments, Solution B also includes additional components such as polyvinyl pyrrolidone, which can inactivate polyphenol inhibitors present in the lysate, and/or EDTA to chelate divalent cations such as, but not limited to $Mg^{2+}$ that can serve as a co-factor for various enzymes that damage nucleic acids.

In some embodiments, the presently disclosed subject matter also provides methods for isolating gDNA from biological material using the compositions disclosed herein. Thus, in some embodiments the presently disclosed methods comprise (a) contacting a sample comprising gDNA with a first solution comprising hydroxide and a detergent under conditions and for a time sufficient to degrade a cell wall, a cell membrane, a nuclear membrane, or combinations thereof, and/or to denature the gDNA; (b) mixing into the solution resulting from step (a) a second solution comprising high salt and sufficient buffering capacity to reduce the pH of the solution to less than 10, thereby producing a neutralized preparation; (c) centrifuging the sample at a speed and for a length of time sufficient to clarify the neutralized preparation; and (d) removing insoluble material from the neutralized and clarified preparation, whereby a solution of gDNA is produced.

IV. Methods for Analyzing and/or Employing Isolated GDNA

The presently disclosed subject matter also provides methods for analyzing gDNA prepared using the methods disclosed herein, as well as for employing the gDNA so prepared in one or more downstream applications. Any analytical and/or other downstream technique that can be employed on gDNA could be performed with the gDNA isolated by the presently disclosed methods using the compositions disclosed herein. The following includes a non-limiting listing of exemplary analytical and/or other downstream techniques for which the gDNA isolated by the presently disclosed methods using the compositions disclosed herein would be appropriate.

IV.A. Methods for PCR, Including Quantitative PCR (qPCR)

In some embodiments, the presently disclosed subject matter provides methods for performing PCR, including but not limited to qPCR, using gDNA prepared by the presently disclosed methods. In some embodiments, the methods comprise providing a gDNA sample prepared by the presently disclosed method and performing PCR under conditions wherein the $C_T$ value can be collected in real-time for quantitative analysis, whereby qPCR of the gDNA sample is performed.

As used herein, the phrase "$C_T$ value" refers to "threshold cycle", which is defined as the "fractional cycle number at which the amount of amplified target reaches a fixed threshold". In some embodiments, it represents an intersection between an amplification curve and a threshold line. The amplification curve is typically in an "S" shape indicating the change of relative fluorescence of each reaction (Y-axis) at a given cycle (X-axis), which in some embodiments is recorded during PCR by a real-time PCR instrument. The threshold line is in some embodiments the level of detection at which a reaction reaches a fluorescence intensity above background. See Livak & Schmittgen (2001) 25 Methods 402-408. It is a relative measure of the concentration of the target in the PCR. Generally, good $C_T$ values for quantitative assays such as qPCR are in some embodiments in the range of 10-40 for a given reference gene.

Additionally, good $C_T$ values for quantitative assays such as qPCR show a linear response range with proportional dilutions of target gDNA.

In some embodiments, qPCR is performed under conditions wherein the $C_T$ value can be collected in real-time for quantitative analysis. For example, in a typical quantitative PCR experiment, DNA amplification is monitored at each cycle of PCR during the extension stage. The amount of fluorescence generally increases above the background when DNA is in the log linear phase of amplification. In some embodiments, the $C_T$ value is collected at this time point.

IV.B. Methods for Performing Genome Analysis

The presently disclosed subject matter also provides in some embodiments methods of performing genome analysis, including but not limited to genetic marker analysis, such as but not limited to genetic marker analysis related to molecular marker assisted breeding and/or selection; locus copy number analysis; zygosity analysis; seed purity assessment based on molecular marker profiles; and/or plant pathogen and/or disease control. In some embodiments, the methods comprise providing a gDNA sample prepared by the presently disclosed method and performing detecting the presence of a genetic marker (including, but not limited to a single nucleotide polymorphism; SNP) present in the gDNA sample. In some embodiments, the detecting methodology includes a PCR reaction on the gDNA sample prepared by the presently disclosed method, wherein the PCR reaction employs one or more oligonucleotide primers designed to detect the presence or absence of a genetic marker of interest.

In some embodiments, the PCR reaction is qPCR employed for determining copy number of a genetic marker in the genome of an individual. Generalized techniques for assessment of copy number can be found in Livak & Schmittgen (2001) 25 Methods 402-408, Abad et al. (2010) 5 Biotechnol J 412-420, D'haene et al. (2010) 50 Methods 262-270, Ji et al. (2012) 14 J Mol Diagnostics 280-285, etc. T GDNA prepared using the compositions and methods of the presently disclosed subject matter can be employed in these exemplary methods. In some embodiments, the assessment of copy number is in the context of determining the number of copies of a transgene in a transgenic cell and/or subject, and in some embodiments the assessment of copy number is in the context of determining the amplification or the loss of a genetic locus such as, but not limited to a gene.

In some embodiments, gDNA prepared using the compositions and methods of the presently disclosed subject matter can be employed in zygosity analysis. As used herein, the phrase "zygosity analysis" refers to any technique that can be used to determine whether a cell, tissue, organ, or a subject is nullizygous, hemizygous, heterozygous, or homozygous for a particular nucleic acid sequence of interest. Generalized techniques for zygosity analysis include, but are not limited to those disclosed in Tesson et al. (2010) 597 Methods Mol Biol 277-285. For example, the gDNA prepared using the compositions and methods of the presently disclosed can be used in subsequent PCR with target- and/or allele-specific assays in zygosity analysis, wherein the DNA prepared using the presently disclosed compositions and/or methods can serve as template for PCR amplification.

In some embodiments, gDNA prepared using the compositions and methods of the presently disclosed subject matter can be employed in analyzing seed purity based on molecular marker profiles. By way of example and not limitation, the gDNA prepared using the compositions and methods of the presently disclosed subject matter can be employed in a molecular marker analysis, and the purity of a given collection of seeds can be determined by identifying whether or not the seeds constitute a single molecular marker profile or if multiple profiles can be identified. In the latter instance, the presence of multiple marker profiles or SNP genotype profiles for one or more selected genes can suggest either heterozygosity in the seeds (e.g., two different alleles at a given locus are present in the seeds in equal proportions), whereas the presence of multiple marker profiles for one or more selected genes can also suggest that the seeds are not isogenic (i.e., comprise a plurality of genomes).

In some embodiments, gDNA prepared using the compositions and methods of the presently disclosed subject matter can be employed in or plant pathogen and/or disease detection and/or monitoring.

EXAMPLES

The following Examples provide illustrative embodiments. Certain aspects of the following Examples are disclosed in terms of techniques and procedures found or contemplated by the present inventors to work well in the practice of the embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Preliminary Experiments to Optimize Reagent Concentrations

A series of experiments were performed in which various concentrations of NaOH, SDS, ammonium acetate (NH$_4$Ac), polyvinylpyrrolidone (PVP40), and/or EDTA were employed in the preparation of gDNA from leaf tissues of maize. The following describes the general procedure that was used for each test.

A sample of two leaf discs, each about 6 mm in diameter, was loaded in a deep well block (Costar 96-well block; Fisher Scientific) containing one steel bead (3/16 inch chrome steel balls; Bearing and Industrial Sales, Inc.) in each well. The block was cooled in a −80° C. freezer for at least one hour, after which the samples were ground while frozen on a Kinetic Laboratory Equipment Company (KLECO) tissue grinder for 1 minute at setting 9 at room temperature (RT).

After grinding, the block was briefly centrifuged in a bench-top centrifuge (Centrifuge 5810R; Eppendorf) to remove tissue debris from the lid. 100 µl of Solution A (see Table 1 below) was then added and the sample was ground for an additional 1 minute at setting 9 using the KLECO tissue grinder at RT. After this second grinding step, the samples were incubated for 3 minutes at RT with occasional inverting. The block was again briefly centrifuged to remove tissue debris from the lid, and 50 µl of Solution B (see Table 1 below) was added to each well. After the addition of Solution B, the block was vigorously inverted 15-20 times at RT. The samples were then centrifuged for 10 minutes at 4000 rpm (3220×g) at 4° C. The supernatant was transferred and then diluted in 1×TE (10 mM Tris-HCl, pH 8.0, 1 mM EDTA).

TABLE 1

Exemplary Compositions for Solutions A and B

| Variable Tested | Amount | | | |
|---|---|---|---|---|
| Solution A | | | | |
| NaOH (M) | 0 | 0.1 | 0.2 | 0.3 |
| SDS (%) | 0 | 0.25 | 0.5 | 1.0 |
| Solution B | | | | |
| NH$_4$Ac (M) | 0 | 3.0 | 4.5 | 6.0 |
| EDTA (mM) | 0 | 2.5 | 5.0 | 10.0 |
| PVP40 (%) | 0 | 0.5 | 1.0 | 2.0 |
| Solution A Volume (µl) | | 60 | 100 | |
| Fold Dilution | 5 (7.5) | 10 | 20 | 40 |

In the following EXAMPLES, ranges and combinations of NaOH and SDS for Solution A listed in Table 1 were tested, and ranges of Solution B components listed in Table 1 were also tested. This series of experiments sought to optimize the concentrations of the individual components of Solutions A and B as well as investigate the effect that different volumes of Solution A and fold dilutions might have on the quality of the nucleic acids isolated by the disclosed methods.

Example 2

Comparison Tests with Respect to Assay Volume at Different Dilutions

Two different volumes of Solution A, 60 µl and 100 µl, were tested. Solution A was 0.2 M NaOH and 0.25% SDS. Solution B was 0.2 M Tris pH 7.5, 3M NH$_4$Ac, 5 mM EDTA, and 1% PVP40. As described in EXAMPLE 1, each of the samples contained two (2) leaf discs of approximately 6 mm in diameter. The protocol was the same as in EXAMPLE 1 except for the different volumes of Solution A employed. As in EXAMPLE 1, the supernatant was transferred and then diluted in 1×TE.

For the present and the following EXAMPLES, a range of dilutions were made of the supernatant. The DNA samples were then used for qPCR. TAQMAN® assays were performed on the endogenous maize gene encoding alcohol dehydrogenase following standard methodology using primers having the sequences disclosed herein as SEQ ID NO: 1 and SEQ ID NO: 2, JUMPSTART™ TAQ READYMIX™ (Sigma-Aldrich), and the ABI PRISM® 7900HT sequence detection system. The results, shown in Table 2, are expressed as $C_T$ values plus or minus one standard deviation. Two samples were prepared for each volume and four replicates of each sample were used for the $C_T$ value calculation in the Table.

TABLE 2

Effect of Volume of Solution A and Sample Dilution on qPCR Analysis*

| Volume of Solution A | Dilution | | | |
|---|---|---|---|---|
| (µl) | 1:5 | 1:10 | 1:20 | 1:40 |
| 60 | 21.6 ± 0.2 | 22.7 ± 0.3 | 23.7 ± 0.2 | 24.7 ± 0.2 |
| 100 | 22.1 ± 0.2 | 23.2 ± 0.3 | 24.2 ± 0.2 | 25.2 ± 0.2 |

*Results are expressed as $C_T$ values following qPCR of the maize alcohol dehydrogenase gene The $C_T$, or threshold cycle, was defined as the intersection between an amplification curve and a threshold line. It was a relative measure of the concentration of the target in the PCR. The $C_T$ value increased with a decreasing amount of template. Generally, good $C_T$ values for quantification were in the range of 10-40 for a given reference gene. Additionally, good $C_T$ values for quantification showed a linear response range with proportional dilutions. The relatively low $C_T$ values in Table 2 indicated that the DNA samples were good for quantitative analysis, starting at 1:5 dilutions, for both volumes of Solution A. The single unit increase of $C_T$ for each dilution (for example, in the samples with 60 µl Solution A, $C_T$=22.7 for the 1:10 dilution, 23.7 for 1:20 dilution, and 24.7 for 1:40 dilution) indicated that this assay was within its linear response range, such that quantitative analysis could be performed. Therefore, the quality of DNA isolated using this method was suitable for qPCR, as well as genotyping and other qualitative analyses.

Example 3

Comparison Tests with Respect to EDTA Concentration in Solution B

To evaluate the contribution of the metal chelator EDTA in the presently disclosed methods, concentrations in the range of 0 to 10 mM EDTA were tested in Solution B. Solution A was the same as in EXAMPLE 2. For this EXAMPLE, Solution B was 0.2 M Tris and various concentrations of EDTA. The methodology was as described in EXAMPLES 1 and 2. As in EXAMPLE 2, the DNA samples clarified by centrifugation were diluted in 1×TE prior to qPCR analysis. qPCR was performed using TAQMAN® assays and the ABI PRISM® 7900HT sequence detection system as described in EXAMPLE 2. Results are expressed as $C_T$ values plus or minus one standard deviation. Results are shown in Table 3. Two samples were prepared for each EDTA concentration, and four replicates of each sample were used for the $C_T$ value calculation in the Table.

TABLE 3

Effect of EDTA Concentration in Solution B on qPCR Analysis*

| EDTA (mM) | Dilution | | |
|---|---|---|---|
| | 1:10 | 1:20 | 1:40 |
| 0 | 25.0 ± 0.2 | 26.6 ± 0.5 | 27.7 ± 0.3 |
| 2.5 | 23.8 ± 0.2 | 25.1 ± 0.1 | 26.1 ± 0.1 |
| 5 | 23.1 ± 0.3 | 24.2 ± 0.2 | 25.4 ± 0.4 |
| 10 | 23.6 ± 0.9 | 24.7 ± 0.1 | 25.8 ± 0.1 |

*Results are expressed as $C_T$ values following qPCR of the maize alcohol dehydrogenase gene At 5 mM EDTA, there was an increase of about 1 $C_T$ value as the sample dilution doubled from 1:10 to 1:20 and again to 1:40. This indicated that the presence of 5 mM EDTA resulted in data that were in the linear response range, which is typically advantageous for quantitative analysis. Therefore, 5 mM was selected as a desirable concentration of EDTA in Solution B.

Example 4

Comparison Tests with Respect to PVP40 Concentration in Solution B

PVP40 is an effective deactivator of polyphenolic compounds, which are commonly present in plant materials and particularly in older tissues. "Older" maize leaves are typically a few months old, and appear dark green or yellowing. This is in contrast to young maize leaf tissue, which is generally no more than a couple weeks old and light green in color.

Polyphenolic compounds are also known to be present in relatively high concentrations in certain crop plants, such as cotton and lettuce, and are further known to be highly inhibitory towards those polymerases that are typically employed in PCR and qPCR.

In this EXAMPLE, various concentrations between 0 to 2.0% of PVP40 were tested in Solution B, which otherwise contained 0.2 M Tris pH 7.5, 5 mM EDTA, and 3M NH$_4$Ac. Solution A was the same as in EXAMPLES 2 and 3. The methodology was as described in EXAMPLE 1.

As in EXAMPLES 2 and 3, the DNA samples clarified by centrifugation were diluted in 1×TE prior to qPCR analysis. qPCR was performed using TAQMAN® assays and the ABI PRISM® 7900HT sequence detection system as described herein above. Results are expressed as $C_T$ values plus or minus one standard deviation. Results are shown in Table 4. As in EXAMPLES 2 and 3, two samples were prepared for each experimental condition, and four replicates of each sample were used for the $C_T$ value calculation in the Table.

TABLE 4

Effect of PVP40 Concentration in Solution B on qPCR Analysis*

| PVP40 (%) | Dilution | | | |
|---|---|---|---|---|
| | 1:7.5 | 1:10 | 1:20 | 1:40 |
| 0 | 25.1 ± 0.5 | 23.3 ± 0.2 | 24.3 ± 0.2 | 25.3 ± 0.1 |
| 0.5 | 24.1 ± 0.3 | 23.4 ± 0.3 | 24.5 ± 0.3 | 25.5 ± 0.3 |
| 1.0 | 22.7 ± 0.2 | 22.8 ± 0.1 | 24.0 ± 0.1 | 25.0 ± 0.2 |
| 2.0 | 23.6 ± 0.4 | 23.1 ± 0.2 | 24.2 ± 0.2 | 25.1 ± 0.2 |

*Results are expressed as $C_T$ values following qPCR of the maize alcohol dehydrogenase gene The addition of PVP40 in Solution B for DNA extraction from maize leaf tissue resulted in significantly lower $C_T$ values, suggesting that appropriate amounts of PVP40 were helpful in purifying gDNA of good quality for qPCR analysis, especially for polyphenol-rich tissues at lower fold dilutions such as, but not limited to at least ten fold dilutions (see Table 4).

Example 5

Comparison Tests with Resect to NH$_4$Ac Concentrations in Solution B

The effect of different NH$_4$Ac concentration in Solution B was tested. Solution A was 0.2 M NaOH and 0.50% SDS. Solution B was 0.2 M Tris pH 7.5, 5 mM EDTA, and 1% PVP40. In this EXAMPLE, concentrations of 0 M, 3 M, 4.5 M, and 6 M NH$_4$Ac were tested. The general methodology was as described in the above EXAMPLES, and the clarified DNA samples were diluted in 1×TE prior to qPCR analysis as in EXAMPLES 2-4.

The results are presented in Table 5. Results are expressed as $C_T$ values plus or minus one standard deviation. As in the previous EXAMPLES, two samples were prepared for each experimental condition, and four replicates of each sample were used for the $C_T$ value calculation in the Table.

TABLE 5

Effect of NH$_4$Ac Concentration in Solution B on qPCR analysis*

| NH$_4$Ac (M) | Dilution | | | |
|---|---|---|---|---|
| | 1:7.5 | 1:10 | 1:20 | 1:40 |
| 0 | >40 | >40 | >40 | 24.9 ± 0.1 |
| 3.0 | 22.8 ± 0.1 | 22.8 ± 0.1 | 23.9 ± 0.1 | 25.0 ± 0.2 |
| 4.5 | 30.7 ± 2.5 | 23.3 ± 0.3 | 24.1 ± 0.3 | 25.1 ± 0.3 |
| 6.0 | 39.6 ± 1.1 | 24.4 ± 0.5 | 23.9 ± 0.2 | 25.0 ± 0.1 |

*Results are expressed as $C_T$ values following qPCR of the maize alcohol dehydrogenase gene These results illustrated that 3.0 NH$_4$Ac and 4.5 M NH$_4$Ac dramatically improved the DNA quality in terms of reduced $C_T$ values and large dynamic range from 1:10 to 1:40 dilution, suggesting that the inclusion of appropriate concentrations of NH$_4$Ac were helpful in purifying gDNA of acceptable quality for qPCR analysis.

Example 6

Comparison Tests with Respect to SDS Concentration in Solution A

In this EXAMPLE, the effect of different SDS concentrations in Solution A was tested. Solution A contained 0.2 M NaOH and either 0%, 0.25%, 0.5%, or 1% SDS. Solution B was 0.2 M Tris pH 7.5, 3 M NH₄Ac, 5 mM EDTA, and 1% PVP40. The general methodology was as described in the above EXAMPLES, and the purified DNA samples were diluted prior to qPCR analysis also as described herein above. The results are expressed as $C_T$ values plus or minus one standard deviation as shown in Table 6. As in the previous EXAMPLES, two samples were prepared for each experimental condition, and four replicates of each sample were used for the $C_T$ value calculation in the Table.

TABLE 6

Effect of SDS Concentration in Solution A on qPCR Analysis*

| SDS (%) | Dilution | | | |
|---|---|---|---|---|
| | 1:5 | 1:10 | 1:20 | 1:40 |
| 0 | 34.5 ± 2.2 | 23.7 ± 0.1 | 24.8 ± 0.2 | 25.6 ± 0.2 |
| 0.25% | 27.2 ± 1.0 | 23.0 ± 0.2 | 24.1 ± 0.2 | 25.1 ± 0.2 |
| 0.5% | 39.4 ± 1.7 | 22.8 ± 0.1 | 23.9 ± 0.2 | 24.9 ± 0.1 |
| 1.0% | 39.5 ± 1.3 | 22.8 ± 0.1 | 23.9 ± 0.1 | 24.9 ± 0.1 |

*Results are expressed as $C_T$ values following qPCR of the maize alcohol dehydrogenase gene For each concentration of SDS, including 0%, the samples for the 1:10 to 1:40 dilution range showed low $C_T$ values and a large dynamic range. This suggested that, for this particular EXAMPLE, SDS might not have been necessary. However, up to 1% SDS did not show negative effects on the qPCR for the 1:10 to 1:40 dilutions of the samples. The high $C_T$ values in the 1:5 dilution, as well as the lack of linearity compared to the other dilutions, indicated that qPCR did not perform desirably for these DNA samples at the 1:5 dilution.

Example 7

Comparison Tests with Respect to NaOH Concentration in Solution A

The effect of NaOH in Solution A was also tested. Solution A was 0.5% SDS plus 0 M, 0.1 M, 0.2 M, or 0.3 M NaOH. Solution B was the same as in EXAMPLE 6. The general methodology was as described herein above examples, and the purified DNA samples were diluted prior to qPCR analysis also as described herein above. The results are expressed as $C_T$ values plus or minus one standard deviation and are shown in Table 7. As in the previous EXAMPLES, two samples were prepared for each experimental condition, and four replicates of each sample were used for the $C_T$ value calculation in the Table.

TABE 7

Effect of NaOH Concentration in Solution A on qPCR Analysis*

| NaOH (M) | Dilution | | | |
|---|---|---|---|---|
| | 1:5 | 1:10 | 1:20 | 1:40 |
| 0 | 37.0 ± 0 | 33.1 ± 1.3 | 28.8 ± 0.8 | 29.8 ± 1.5 |
| 0.1M | 27.8 ± 0.7 | 25.6 ± 0.2 | 26.8 ± 0.5 | 27.7 ± 0.2 |
| 0.2M | 27.9 ± 0.5 | 25.0 ± 0.2 | 26.1 ± 0.2 | 27.3 ± 0.2 |
| 0.3M | 29.9 ± 2.5 | 25.1 ± 0.0 | 26.2 ± 0.1 | 27.3 ± 0.1 |

*Results are expressed as $C_T$ values following qPCR of the maize alcohol dehydrogenase gene The results indicated that the addition of NaOH in Solution A was important for qPCR. The results indicated that 0.1 M to 0.3 M NaOH in Solution A provided for low $C_T$ values and a large dynamic range, from 1:10 to 1:40 dilutions. The results further indicated that qPCR did not perform as desired for most DNA samples at the 1:5 dilution.

Example 8

Comparison Tests with Respect to Both NaOH and SDS Concentrations in Solution A

Building on the results of EXAMPLES 6 and 7, this EXAMPLE tested whether additive or synergistic effects could be observed when 0.5% SDS and 0.2 M NaOH were employed together in Solution A compared to when these components were employed individually. Solution B was the same as in EXAMPLES 6 and 7. The general methodology was as described herein above, and the purified DNA samples were diluted prior to qPCR analysis as also described previously. The results are expressed as $C_T$ values plus or minus one standard deviation in Table 8. As in the previous EXAMPLES, two samples were prepared for each experimental condition, and four replicates of each sample were used for the $C_T$ value calculation in the Table.

TABLE 8

Effect of NaOH and SDS Concentration in Solution A on qPCR Analysis*

| Combination | Dilution | | | |
|---|---|---|---|---|
| | 1:7.5 | 1:10 | 1:20 | 1:40 |
| 0.5% SDS only | 25.1 ± 1.1 | 25.3 ± 0.7 | 26.2 ± 0.4 | 26.3 ± 0.4 |
| 0.2M NaOH only | 23.1 ± 0.2 | 23.5 ± 0.2 | 24.7 ± 0.1 | 25.7 ± 0.1 |
| 0.2M NaOH + 0.5% SDS | 22.8 ± 0.1 | 22.8 ± 0.1 | 23.9 ± 0.1 | 25.0 ± 0.2 |

*Results are expressed as $C_T$ values following qPCR of the maize alcohol dehydrogenase gene The results showed that the NaOH+SDS in combination resulted in here significantly lower $C_T$ values as compared to those observed when either 0.5% SDS or 0.2 M NaOH were employed individually. Surprisingly, this suggested that the quality of gDNA extracted using both NaOH and SDS together was higher than that of gDNA extracted using either chemical individually.

Example 9

Tests with Respect to DNA Stability

The stability of gDNA prepared by the method was also examined. Solution A was 0.2 M NaOH and 0.25% SDS, and Solution B was the same as that employed in EXAMPLES 6-8. The general methodology was as described in the above EXAMPLES, and the purified DNA samples were diluted prior to qPCR analysis, also as previously described.

Once the DNA sample was diluted into 1×TE, qPCR was performed as described in the previous EXAMPLES. This first qPCR performed immediately after the DNA was prepared was notated as week 0. Over 8 weeks, the DNA samples were stored at 4° C. and tested by qPCR weekly. qPCR was performed as in the above EXAMPLES. Results are expressed as $C_T$ values plus or minus one standard deviation. Representative results are shown in Table 9. Two out of eight samples and four replicates of each sample were used for the $C_T$ values calculated in the table.

TABLE 9

DNA stability Measured as Suitability as a
Template for qPCR analysis*

| | Dilution | |
| Time Course | 1:10 | 1:20 |
| --- | --- | --- |
| Week 0 | 24.3 ± 0.1 | 25.6 ± 0.1 |
| Week 1 | 24.0 ± 0.1 | 25.5 ± 0.2 |
| Week 3 | 24.1 ± 0.1 | 25.6 ± 0.1 |
| Week 8 | 24.0 ± 0.1 | 25.5 ± 0.1 |

*Results are expressed as $C_T$ values following qPCR of the maize alcohol dehydrogenase gene The near constant $C_T$ values after 4° C. storage for up to 8 weeks demonstrated stability of the DNA and its suitability for qPCR over the course of 8 weeks.

Example 10

GDNA Extraction Method Used for SNP Genotyping of Rice Seeds

To illustrate that the presently disclosed methods could be used for more than the one generalized application described in the previous EXAMPLES, rice seeds were used as a source for DNA extraction, and an allelic discrimination (SNP) assay was performed on the extracted DNA samples. A population of 30 different rice varieties, with 3 representative seeds from each, was examined. Prior to extraction, the rice seeds were incubated at room temperature overnight in distilled water. DNA from the seeds was then extracted according to method described in EXAMPLE 1. A single seed was used for each sample. Solution A was 0.2 M NaOH and 0.25% SDS. Solution B was 0.2 M Tris-HCl, pH 7.5, 3.0 M $NH_4Ac$, 5 mM EDTA, and 1% PVP40. Samples were diluted ten-fold in 1×TE buffer. For the SNP genotyping, a negative control, which contained 1×TE buffer with no DNA, was used. The SNP genotyping was performed using 2× Master Mix (JUMPSTART™ TAQ READYMIX™), 2 primers specific to the two SNP's being tested, 2 probes, DNA prepared from the disclosed DNA extraction method, and an ABI 9700 thermal cycler. Using the Sequence Detection System (SDS) software, allele calls were made based on the fluorescence for the two dyes measured in each sample.

The results are shown in FIG. 1. The negative samples, which did not contain DNA, are shown in black crosses in the lower left quadrant of FIG. 1, and are represented as an "undetermined" result. The experimental results showed that the majority of the seeds where homozygous for allele 2 (clustered blue circles in the upper left quadrant of FIG. 1), with 7 samples heterozygous (clustered green circles in the upper right quadrant of FIG. 1), and only a few samples homozygous for allele 1 (clustered red circles in the lower right quadrant of FIG. 1). The discrete, tight clustering is indicative of the high quality of the DNA used for the reactions.

Discussion of the Examples

In sum, the EXAMPLES described above demonstrated the optimization of the DNA preparation method disclosed within. The results for each solution component indicated good $C_T$ values could be obtained using a range of concentrations for the solution components as well as a range for sample dilutions prior to qPCR. As observed for each EXAMPLE, for each component there was a range of concentration and dilution that provided for good qPCR analysis.

EXAMPLE 2 indicated that using 60 µl or 100 µl of Solution A, with sample dilutions of 1:5 to 1:40, were good for qPCR analysis.

EXAMPLE 3 indicated that 5 mM EDTA in Solution B, with sample dilutions of 1:10 to 1:40, were good for qPCR analysis.

EXAMPLE 4 indicated that 0-2% PVP40 in Solution B, with sample dilutions of 1:10 to 1:40, were good for qPCR analysis.

EXAMPLE 5 indicated that 3.0-4.5 M $NH_4Ac$ in Solution B, with sample dilutions of 1:10 to 1:40, were good for qPCR analysis.

EXAMPLE 6 indicated that 0-1.0% SDS in Solution A, with sample dilutions of 1:10 to 1:40, were good for qPCR analysis.

EXAMPLE 7 indicated that 0.1-0.3 M NaOH in Solution A, with sample dilutions of 1:10 to 1:40, were good for qPCR analysis.

EXAMPLE 8 indicated that 0.5% SDS and 0.2 M NaOH, with sample dilutions of 1:10 to 1:40, were good for qPCR analysis.

The presently disclosed methods for preparing gDNA were also compared to different existing gDNA preparation procedures as described below. From these experiments it was determined that DNA quality from the presently disclosed methods may be higher than for the other methods tested in terms of tight replicates (small standard deviation) in qPCR and clear allelic discrimination in genotyping, total DNA yield was 3-5 fold higher according to the quantitative analysis by qPCR, very short duration from sample to ready DNA makes the throughput superior to any existing HT method, running costs were very low because of simple steps and common chemicals, the presently disclosed method employed a minimum of manipulations, and was user- and environment-friendly For example, as compared to the CTAB method of Japelaghi et al., 2011, the presently disclosed methods were far superior for high throughput applications, provided gDNA of similar if not superior quality, could be performed in substantially less time, and avoided the use of hazardous chemicals.

As compared to the SDS-isopropanol method of Kotchoni & Gachomo, 2009, the presently disclosed methods avoided the need to precipitate and dry the gDNA before use, resulted in substantially fewer inhibitors of downstream applications being present in the gDNA preparation, and was superior as a high throughput methodology.

As compared to the proteinase K method of Dilworth & Frey, 2000, the presently disclosed methods provided greater yields of higher quality gDNA and avoided the use of proteinase K, which can inhibit downstream applications and is a relatively expensive reagent.

And finally, as compared to the hydroxide/acetate method of Porcar et al., 2007, the presently disclosed methods provided gDNA of substantially higher quality both with respect to the gDNA per se as well as provided a preparation that lacked the many inhibitors of downstream applications that typically remain in the gDNA prepared using the hydroxide/acetate method of Porcar et al., 2007.

In contrast, the presently disclosed methods represent quick, simple, inexpensive, and high throughput gDNA extraction methods. The quantity and quality of gDNA recovered are typically at least as high or higher than that from standard techniques for HT analysis and produce gDNA that is suitable for quantitative analysis by real-time quantitative PCR. The particular combination of reagents employed in the presently disclosed methods has multiple functions in extracting high quality gDNA, resulting in effective elimination of contaminants and inhibitors. For example, the presently disclosed methods: 1) generate more efficient cell lysis and gDNA release via the combination and synergy of alkali and SDS, resulting in gDNA that is easily accessible to primers and polymerases in downstream applications; 2) employ high salt to precipitate SDS-proteins, polysaccharides, and other macromolecular complexes that can inhibit downstream applications; 3) include PVP40 and EDTA to remove polyphenols and stabilize the isolated gDNA; and 4) avoid the use of hazardous solvents, PCR inhibitory chemicals, and various other costly reagents and materials.

In addition to the maize leaf tissue tested above, this method has also been used successfully on a variety of tissues and seeds from other plants including soybean leaf, sugarcane leaf, wheat leaf, rice seeds, cotton leaf, maize seeds, soybean seeds, and cotton seeds. Real-time quantitative results typically give $C_T$ values in the range of 22 to 25 at 1:10 dilution of the DNA samples, indicative of the high quality of the DNA extracted and demonstrating the broad applicability of the presently disclosed methods to a number of plant and tissue types.

Additionally, the presently disclosed methods provide further advantages relative to standard gDNA preparation methods. First, the presently disclosed methods can be employed for most if not all sources of gDNA, and yield gDNA that is of high quality and has been shown to be stable for at least 8 weeks when stored at 4° C. The presently disclosed methods are also easily adaptable to high-throughput procedures and are very economical, using reagents that are relatively inexpensive. And finally, the reagents employed are user- and environment-friendly.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Ausubel et al. (eds.) (1988) *Current Protocols in Molecular Biology*. Greene Pub. Associates; Wiley-Interscience, New York, N.Y., United States of America.

Ausubel et al. (eds.) (1999) *Short Protocols in Molecular Biology (Fourth Edition)*. John Wiley & Sons, New York, N.Y., United States of America.

Bailes et al. (2007) An inexpensive, simple protocol for DNA isolation from blood for high-throughput genotyping by polymerase chain reaction or restriction endonuclease digestion. *Poultry Sci* 86:102-106.

Birnboim & Doly (1979) A rapid alkaline extraction procedure for screening recombinant plasmid DNA. *Nucleic Acids Res* 7:1513-1523.

Collard et al. (2007) Evaluation of 'quick and dirty' DNA extraction methods for marker-assisted selection in rice (*Oryza sativa* L.). *Plant Breeding* 126:47-50.

Cullen & Hirsch (1998) Simple and rapid method for direct extraction of microbial DNA from soil for PCR. *Soil Biol Biochem* 30:983-993.

Demeke & Jenkins (2010) Influence of DNA extraction methods, PCR inhibitors and quantification methods on real-time PCR assay of biotechnology-derived traits. *Anal Bioanal Chem* 396:1977-1990.

Dilworth & Frey (2000) A rapid method for high throughput DNA extraction from plant material for PCR amplification. *Plant Mol Biol Rep* 18:61-64.

Japelaghi et al. (2011) Rapid and efficient isolation of high quality nucleic acids from plant tissues rich in polyphenols and polysaccharides. *Mol Biotechnol* 49:129-137.

Kotchoni & Gachomo (2009) A rapid and hazardous reagent free protocol for gDNA extraction suitable for genetic studies in plants. *Mol Biol Rep* 36:1633-1636.

Michiels et al. (2003) Extraction of high quality gDNA from latex containing plants. *Anal Biochem* 315:85-89.

Murray & Thompson (1980) Rapid isolation of high molecular weight plant DNA. *Nucleic Acids Res* 8:4321-4326.

Pafundo et al. (2011) Comparison of DNA extraction methods and development of duplex PCR and real-time PCR to detect tomato, carrot, and celery in food. *J Agric Food Chem* 59:10414-10424.

PCT International Patent Application Publication Nos. WO 1996/018731; WO 2009/014415.

Porcar et al. (2007) A simple DNA extraction method suitable for PCR detection of genetically modified maize. *J Sci Food Agric* 87:2728-2731.

Qiang et al. (2004) A simple protocol for isolating gDNA from Chestnut Rose (*Rosa roxburghii* Tratt) for RFLP and PCR Analysis. *Plant Mol Biol Rep* 22:301-302.

Sambrook & Russell (2001) *Molecular Cloning, A Laboratory Manual (Third Edition)*. Cold Spring Harbor Laboratory Press, Cold Spring Harbor, N.Y., United States of America.

Sharma et al. (2008) A simple and efficient method for extraction of gDNA from tropical tuber crops. *African J Biotechol* 7:1018-1022.

Tan & Yiap (2009) DNA, RNA, and protein extraction: the past and the present. *J Biomed Biotechnol*, Article ID 2009:574398, 10 pages.

Wen & Deng (2002) The extraction of gDNA from five species of *Rosa*. *Seed* 126:18-21.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for isolating gDNA suitable for qPCR from a biological material, the method consisting of:
   (a) contacting a sample comprising gDNA with a first solution comprising 0.1-0.3 M sodium hydroxide and 0.25-0.5% SDS (w/v) under conditions and for a time sufficient to degrade a cell wall, a cell membrane, a nuclear membrane, or combinations thereof, and/or to denature the gDNA;
   (b) mixing into the solution resulting from step (a) a second solution comprising about 0.2 M Tris pH 7.5 and 3-4.5 M ammonium acetate;
   (c) centrifuging the sample at a speed and for a length of time sufficient to clarify the neutralized preparation; and
   (d) removing insoluble material from the neutralized and clarified preparation,
   whereby a solution of gDNA is produced, which is suitable for qPCR.

2. The method of claim 1, wherein the sample comprises ground plant tissue, optionally ground leaf tissue, ground seed, ground grain, or any combination thereof.

3. The method of claim 1, wherein the centrifuging step comprises centrifuging the neutralized and clarified preparation for about 10 minutes at about 3200×g.

4. The method of claim 1, wherein the removing step comprises transferring a supernatant comprising the gDNA that results from the centrifuging step to a new container.

5. The method of claim 4, further comprising adjusting the supernatant to 10 mM Tris.

6. The method of claim 1, wherein the removing step comprising transferring the clarified and neutralized preparation to a new container.

7. The method of claim 6, further comprising diluting the clarified and neutralized preparation in TE.

8. A method for performing a quantitative polymerase chain reaction (qPCR) of a gDNA sample, the method comprising:
   (a) providing a gDNA sample prepared by the method of claim 1; and
   (b) performing PCR under conditions wherein the $C_T$ value can be collected for quantitative analysis, whereby qPCR of the gDNA sample is performed.

9. A method for genotyping a gDNA sample, the method comprising:
   (a) providing a gDNA sample prepared by the method of claim 1; and
   (b) performing a molecular assay using at least two primers and two allele-specific probes, wherein end-point signal levels show zygosity status on a 2-D allelic discrimination plot.

10. The method of claim 9, wherein the molecular assay comprises a single nucleotide polymorphism (SNP) assay.

11. A method for determining a haplotype of a cell with respect to a gene of interest, the method comprising:
    (a) providing a gDNA sample isolated from the cell prepared by the method of claim 1, wherein the gDNA sample comprises gDNA comprising the gene of interest;
    (b) performing quantitative PCR (qPCR) on the gDNA sample with one or more nucleic acid reagents that are designed to discriminate between at least two alleles of the gene of interest; and
    (c) analyzing products from the qPCR,
    wherein a haplotype of the cell with respect to the gene of interest is determined.

12. The method of claim 11, wherein the one or more nucleic acid reagents comprise at least two sets of oligonucleotide primers, a first set of which is specific for a first allele of the gene of interest and a second set of which is specific for a second allele of the gene of interest.

13. The method of claim 1, wherein the second solution further comprises 2.5-10.0 mM EDTA.

14. The method of claim 1, wherein the second solution further comprises 0.5-2.0% PVP40.

15. The method of claim 1, wherein the first solution comprises 0.2 M sodium hydroxide.

* * * * *